US006587482B1

(12) United States Patent
Kato

(10) Patent No.: US 6,587,482 B1
(45) Date of Patent: Jul. 1, 2003

(54) LASER APPARATUS

(75) Inventor: Katsuhiro Kato, Okazaki (JP)

(73) Assignee: Nidek Co., Ltd., Gamagori (JP)

( * ) Notice: Subject to any disclaimer, the term of this patent is extended or adjusted under 35 U.S.C. 154(b) by 93 days.

(21) Appl. No.: 09/665,331

(22) Filed: Sep. 19, 2000

(30) Foreign Application Priority Data

Sep. 21, 1999 (JP) .......................................... 11-266839

(51) Int. Cl.[7] .............................................. H01S 3/10
(52) U.S. Cl. .............................................. 372/9; 606/10
(58) Field of Search ........................... 372/29.01, 38.02, 372/109, 9; 606/10–12

(56) References Cited

U.S. PATENT DOCUMENTS

| 6,149,643 | A | * | 11/2000 | Herekar et al. | ................. | 606/5 |
| 6,165,170 | A | * | 12/2000 | Wynne et al. | .................. | 606/9 |
| 6,316,234 | B1 | * | 11/2001 | Bova | ....................... | 435/173.7 |
| 6,346,100 | B1 | * | 2/2002 | Tano et al. | .................... | 606/10 |
| 6,383,178 | B1 | * | 5/2002 | Abe | ............................. | 606/11 |

FOREIGN PATENT DOCUMENTS

JP    10-283152    10/1998

* cited by examiner

*Primary Examiner*—Paul Ip
*Assistant Examiner*—Davienne Monbleau
(74) *Attorney, Agent, or Firm*—Oliff & Berridge PLC

(57) ABSTRACT

A laser apparatus for irradiating an object to be irradiated with a laser beam emitted from a laser source is disclosed. The laser apparatus includes a display provided with a screen for displaying laser irradiation conditions, the display being a touch panel type capable of detecting a touch position on the screen; an input device for inputting a signal to start laser irradiation; a mode selector for selecting one of an irradiation ready mode of enabling the laser irradiation when the signal is input from the input device and a standby mode of locking the laser irradiation even when the signal is input from the input device; and a controller for controlling the laser irradiation in accordance with the mode selected by the mode selector, and locking the laser irradiation when detects a touch within a predetermined area on the screen of the display during the laser irradiation.

4 Claims, 3 Drawing Sheets

LASER APPARATUS

BACKGROUND OF THE INVENTION

1. Field of the Invention

The present invention relates to a laser apparatus for irradiating an object to be irradiated with a laser beam.

2. Description of Related Art

As a laser apparatus for irradiating an object to be irradiated with a laser beam emitted from a laser source, there is a laser treatment apparatus that irradiates an affected part of a patient with a treatment laser beam to treat the affected part. Such the laser apparatus is so configured as to have two operating statuses; an irradiation-ready status (hereinafter referred to as a READY mode) in which laser irradiation is enabled when a laser irradiation start signal (a trigger signal) is entered and a standby status (hereinafter referred to as a STANDBY mode) in which laser irradiation is locked even when a laser irradiation start signal is entered.

The two operating modes can normally selectively be switched at the push of predetermined keys on a control panel. Accordingly, in switching from the READY mode to the STANDBY mode, an operator must search and push an appropriate key for switching to the STANDBY mode from among many keys on the control panel. This would be troublesome to the operator. In an emergency where operators and assistants have to quickly react, particularly, it would be difficult for them to promptly search and press an emergency stop button and the key for switching to the STANDBY mode.

SUMMARY OF THE INVENTION

The present invention has been made in view of the above circumstances and has an object to overcome the above problems and to provide a laser apparatus capable of correctly easily switching from a READY mode to a STANDBY mode.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided a laser apparatus for irradiating an object to be irradiated with a laser beam emitted from a laser source, the laser apparatus including: a display serving as display means provided with a screen for displaying laser irradiation conditions, the display being a touch panel type capable of detecting a touch position on the screen; input means for inputting a signal to start laser irradiation; mode selection means for selecting one of an irradiation ready mode of enabling the laser irradiation when the signal is input from the input means and a standby mode of locking the laser irradiation even when the signal is input from the input means; and control means for controlling the laser irradiation in accordance with the mode selected by the mode selection means, and locking the laser irradiation when detects a touch within a predetermined area on the screen of the display during the laser irradiation.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

Figure 1:
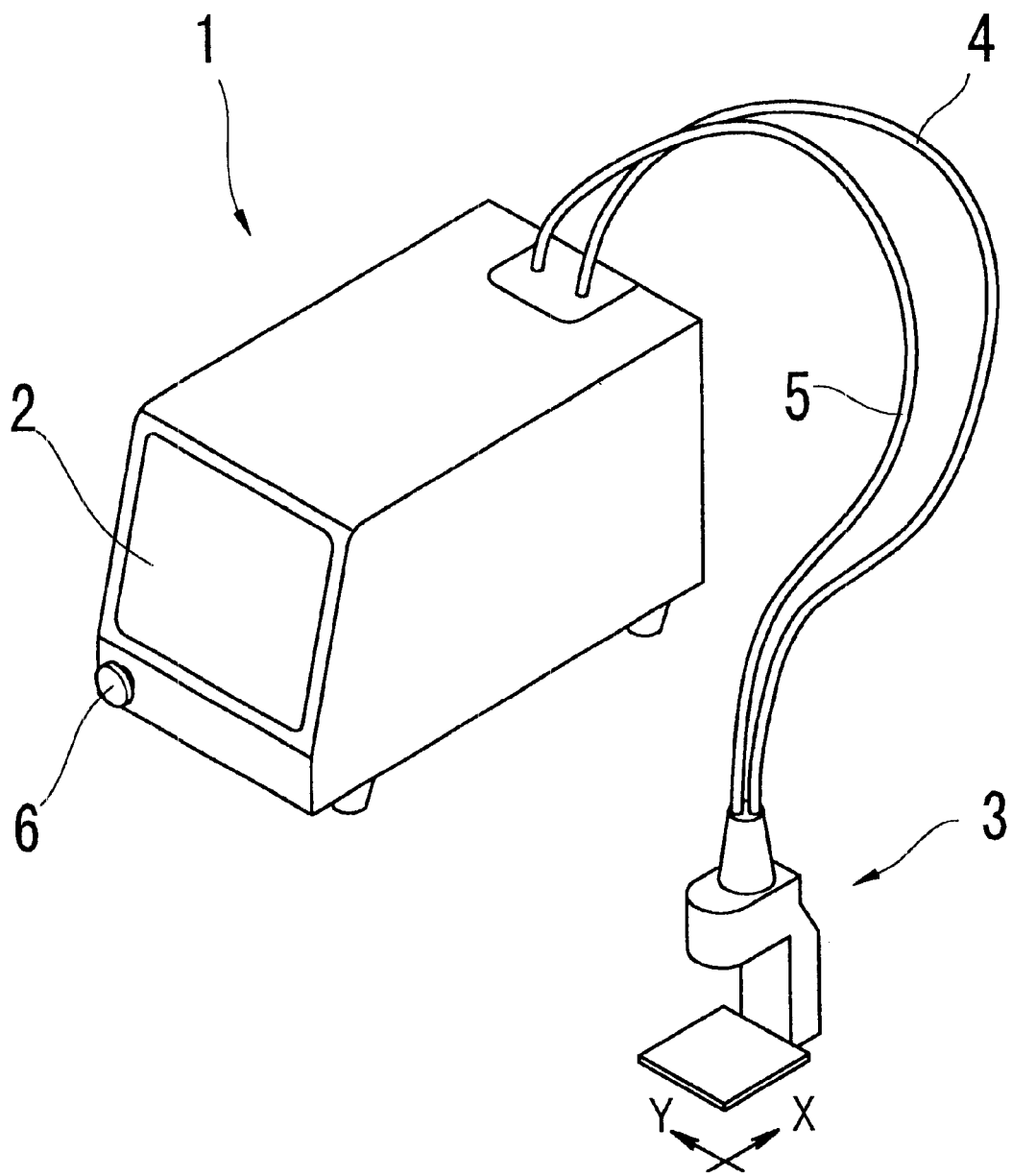
FIG. 1 is a schematic perspective view of a laser apparatus in an embodiment according to the present invention.

A detailed description of a preferred embodiment of a laser apparatus embodying the present invention will now be given referring to the accompanying drawings. FIG. 1 is a schematic perspective view of the laser apparatus in the present embodiment.

A main unit 1 of the laser apparatus is provided at its front with a large-sized liquid crystal display (hereinafter referred to as LCD) 2 of a touch panel-type for displaying various laser irradiation conditions and other. It is to be noted that the touch panel in the present embodiment has a resistance membrane system (which may be either a digital or analog type) capable of detecting a touch position of a finger of an operator in X- and Y-directions (coordinates) of the panel. The thus configured touch panel will show no react even if for example clothes of the operator slightly touch the panel. The main unit 1 is also provided with a fiber cable 4 and a communication cable 5 which are extended from the top of the main unit 1 to a hand piece 3. An emergency stop button 6 is provided at the front face of the main unit 1. At the push of this button 6, supply of electric power to the main unit 1 is shut down.

Figure 2:
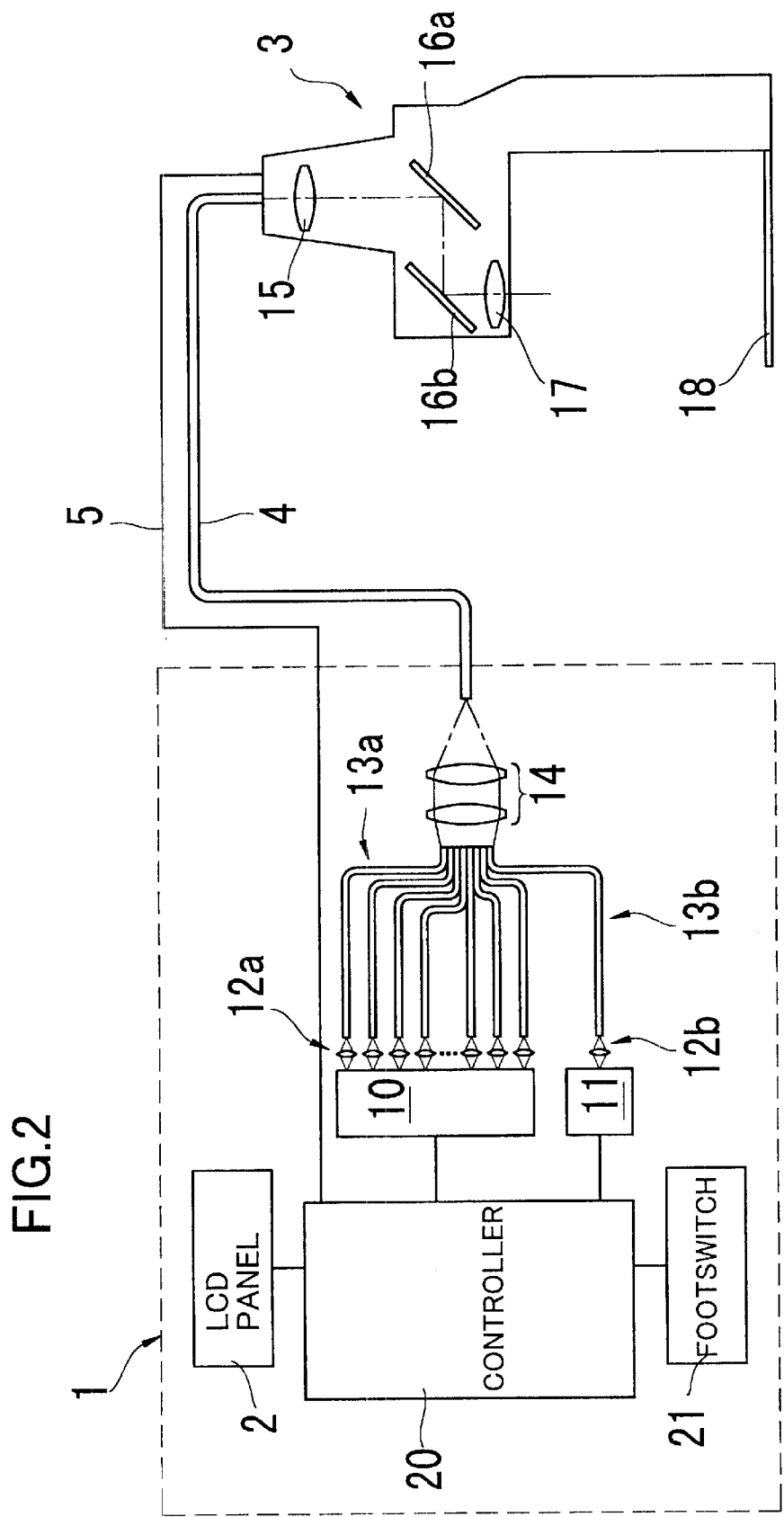
FIG. 2 is a schematic structural view of a main part of an optical system and a control system of the laser apparatus in the embodiment.

FIG. 2 is a schematic structural view of the main part of an optical system and a control system of the laser apparatus. A laser source 10 is constructed of a plurality of diode laser sources each of which emits a treatment laser beam (hereinafter simply referred to as a treatment beam) that is a near-infrared light having a wavelength in the range of 800–820 nm in the present embodiment. This treatment beam is useful for treatments such as laser depilation in which a laser beam is irradiated to hair roots to cauterize them for depilation. The treatment beams emitted from the laser source 10 are condensed by condensing lenses 12a and introduced into the entrance ends of fibers 13a. The emergence ends of the fibers 13a are bound into a bundle as shown in FIG. 2, thereby allowing emission of a treatment beam of high power.

A laser source 11 emits an aiming laser beam (hereinafter simply referred to as an aiming beam) that is a red visible laser beam having a wavelength in the range of 620–650 nm in the present embodiment. The aiming beam emitted from the laser source 11 is condensed by a condensing lens 12b and introduced into the entrance end of a fiber 13b. The emergence end of the fiber 13b is bound with those of the fibers 13a, whereby to make the aiming beam coaxial with the treatment beam.

The treatment beam and the aiming beam emerged from the emergence ends (i.e., fiber bundle portions) of the bound fibers 13a and 13b are then condensed by a group of condensing lenses 14 and introduced into a fiber cable 4. This fiber cable 4 is connected to the hand piece 3. Thus, the treatment beam and the aiming beam are introduced into the hand piece 3 through the fiber cable 4.

Galvano-mirrors 16a and 16b are disposed in the hand piece 3. These galvano-mirrors 16a and 16b are driven for causing the treatment beam and the aiming beam to scan a wide area. That is, the treatment beam and the aiming beam introduced into the hand piece 3 are made into parallel luminous flux by a collimator lens 15, moved or swung in X- and Y-directions by the galvano-mirrors 16a and 16b, and thus concentrated on a part to be treated by a condensing lens 17.

Numeral 18 is a glass plate which will be placed on the treatment part in direct contact therewith during treatment. This glass plate 18 is arranged at the condensing point of the beams by the condensing lens 17, thus bringing the condensing point into correspondence with the treatment part. The size of the glass plate 18 is so designed to cover all the area to be scanned by the treatment beam and the aiming beam. In treating, an operator holds the hand piece 3 with the glass plate 18 pressed against the treatment part so that the surface of this treatment part becomes equally flat, whereby to uniformly perform laser irradiation to the part.

Numeral 20 is a controller for controlling the whole apparatus. This controller 20 is mainly connected with the LCD 2, the galvano-mirrors 16a and 16b through the communication cable 5, and a footswitch 21 for generating a laser irradiation start signal (a trigger signal).

Figure 3:
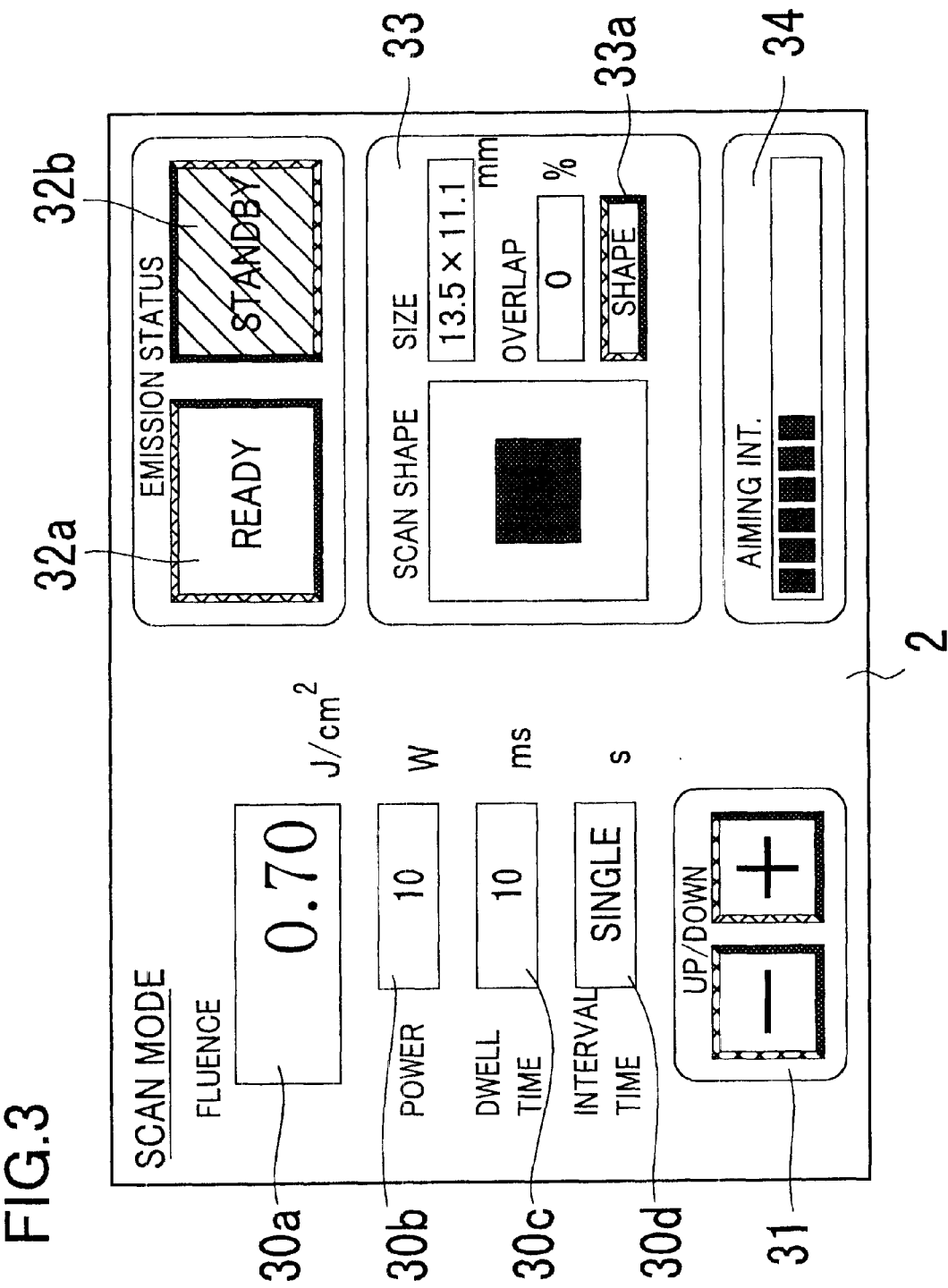
FIG. 3 is an example of a screen of a liquid crystal display of the laser apparatus for setting laser irradiation conditions in the embodiment.

FIG. 3 is an example of a screen of the LCD 2 for setting of laser irradiation conditions. In the left section of the screen, there are arranged an energy density display section 30a which indicates the energy density (J/cm$^2$) of the treatment beam, an irradiation power display section 30b which indicates the irradiation power (W) of the treatment beam, an irradiation time display section 30c which indicates the irradiation time (ms) of the treatment beam, an interval time display section 30d which indicates the interval time (s) in repetitive irradiation, and others.

In the right section of the screen, on the other hand, there are arranged a READY key 32a for selecting a READY mode, a STANDBY key 32b for selecting a STANDBY mode, a scanning area information display section 33 which displays the information on an area to be scanned by the treatment beam (shape, size, etc. of the scanning area), an aiming light quantity display section 34 which indicates the luminous intensity of the aiming beam, and others.

If requiring changing of the laser irradiation conditions, the operator touches one of the display sections 30a–30d, 33, 34 on the screen to select an option or item to be changed, and presses UP/DOWN keys 31 to increase or decrease a set value of the selected option to a desired value. For the shape of the scanning area, the operator presses a SHAPE key 33a in the display section 33 to select a desired one.

Operation of the laser apparatus having the above configuration will be explained below.

When a surgeon or assistant (which will hereinafter be referred to as an operator) turns on the power of the laser apparatus, the controller 20 runs diagnostic checks on itself before startup. Upon startup, the STANDBY mode is established. In this mode, the STANDBY key 32b is displayed in a bright color, e.g., orange, while the READY key 32a in a dark color, e.g., gray. Such the keys 32a and 32b allow the operator to easily recognize the current operating mode. In the STANDBY mode, even when the controller 20 receives a trigger signal from the footswitch 21 depressed, the controller 20 does not supply power to the laser source 10. Thus the treatment beam is not emitted.

Subsequently, the operator controls the keys on the LCD 2 to set the laser irradiation conditions as needed. After completion of preparation for laser irradiation, the operator pushes the READY key 32a to place the apparatus in the READY mode. Upon turn-on of the READY key 32a, the controller 20 performs laser a power check (calibration) to detect whether the irradiation power is a predetermined value. When it is determined that the irradiation power is proper, the apparatus is put into the READY mode. In the READY mode, the READY key 32a is displayed in a bright color, e.g., blue, while the STANDBY key 32b is displayed in a dark color, e.g., gray. In this mode, when the controller 20 receives a trigger signal from the footswitch 21, it supplies power to the laser source 10 to emit the treatment beam.

After confirming that the READY mode is established, the operator depresses the footswitch 21. In response to the trigger signal from the footswitch 21, the controller 20 causes the laser source 10 to emit the treatment beam under the set irradiation conditions such as the irradiation power. The controller 20 simultaneously drives the galvano-mirrors 16a and 16b to cause the treatment beam to scan the predetermined scanning area (shape, size, etc.), thereby irradiating the treatment part.

After the treatment is completed or when changing the laser irradiation conditions is required, the operator has only to touch the screen of the LCD 2. This establishes the STANDBY mode. It is to be noted that the operator may touch any portion or position on the screen of the LCD 2 besides the keys arranged on the LCD 2. During the READY mode, the controller 20 recognizes the whole area of the screen of the LCD 2 as a STANDBY key to switch from the READY mode to the STANDBY mode. If any portion except the STANDBY key 32b is touched, therefore, the controller 20 acts in the same manner that the STANDBY key 32b is exactly touched.

In the READY mode, as mentioned above, the simple control of touching any portion or position on the LCD 2 by the operator makes it possible to easily switch to the STANDBY mode. Accordingly, the need for searching the STANDBY key 32b can be eliminated, which can reduce labors of the operator. If a larger LCD 2 is used, its operability can be more improved. In the case of needing emergency stop of the laser irradiation because of some troubles in the patient or operator, the laser irradiation can be stopped with the touch of the screen of the LCD 2 having a wide area by the operator without a search and push of the emergency button 6. Thus, the operator can correctly easily react in case of emergency.

As described above, according to the above embodiment, the laser apparatus can properly easily be switched from the READY mode to the STANDBY mode.

The present invention may be embodied in other specific forms without departing from the spirit or essential characteristics thereof.

It is to be noted that the area of the screen of the LCD 2 (the area to be recognized as a STANDBY key) for switching the apparatus from the READY mode to the STANDBY mode is sufficient if it is larger than at least the STANDBY key 32b. Preferably, the area is determined to be larger including the display sections 30a–30d used as condition setting keys, the key 31, and others. More preferably, the area recognized as a STANDBY key is determined to be the whole screen of the LCD 2 as in the above embodiment. However, the area is not strictly limited to the whole screen. The area is sufficient if including most of the main area serving as a touch panel.

In the above embodiment, the controller 20 does not supply power to the laser source 10 during the STANDBY mode to thereby lock laser irradiation. Alternatively, a shutter may be inserted on the beam path to lock laser irradiation.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A laser apparatus for irradiating an object to be irradiated with a laser beam emitted from a laser source, the laser apparatus including:

a touch panel display provided with a screen on which touch keys for setting laser irradiation conditions and the set laser irradiation conditions are displayed, the entire screen being a touch key for stopping laser irradiation;

input means for inputting a signal to start laser irradiation;

mode selection means for selecting one of an irradiation ready mode of enabling the laser irradiation when the signal is input from the input means and a standby mode of locking the laser irradiation even when the signal is input from the input means; and control means for controlling the laser irradiation in accordance with the mode selected by the mode selection means and the signal input from the input means and stopping the laser irradiation by touching anywhere on the entire screen, even when the irradiation ready mode is selected and the signal is input.

2. The laser apparatus according to claim 1, wherein the mode selection means includes a touch key for selecting one of the irradiation ready mode and the standby mode displayed on the screen for the display.

3. The laser apparatus according to claim 1, wherein the mode selection means includes a touch key for selecting one of the irradiation ready mode and the standby mode displayed on the screen of the display.

4. The laser apparatus according to claim 1, wherein the control means stops the laser irradiation and changes from the laser irradiation mode to the standby mode by touching anywhere on the entire screen, even when the irradiation ready mode is selected and the signal is input.

* * * * *